United States Patent
Ren et al.

(10) Patent No.: US 10,600,992 B2
(45) Date of Patent: Mar. 24, 2020

(54) PACKAGE STRUCTURE, METHOD FOR MANUFACTURING THE SAME, METHOD FOR DETECTING PACKAGE DEFECT, OLED DEVICE AND DISPLAY APPARATUS

(71) Applicants: BEIJING BOE DISPLAY TECHNOLOGY CO., LTD., Beijing (CN); BOE TECHNOLOGY GROUP CO., LTD., Beijing (CN)

(72) Inventors: Jinyu Ren, Beijing (CN); Guojing Ma, Beijing (CN); Qi Wang, Beijing (CN)

(73) Assignees: BEIJING BOE DISPLAY TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 16/144,085

(22) Filed: Sep. 27, 2018

(65) Prior Publication Data

US 2019/0189951 A1    Jun. 20, 2019

(30) Foreign Application Priority Data

Dec. 15, 2017 (CN) .......................... 2017 1 1350463

(51) Int. Cl.
| | |
|---|---|
| *H01L 51/52* | (2006.01) |
| *H01L 51/56* | (2006.01) |
| *G01N 27/12* | (2006.01) |
| *H01L 51/00* | (2006.01) |

(52) U.S. Cl.
CPC ........ *H01L 51/524* (2013.01); *G01N 27/121* (2013.01); *H01L 51/0031* (2013.01); *H01L 51/5203* (2013.01); *H01L 51/5246* (2013.01); *H01L 51/56* (2013.01)

(58) Field of Classification Search
CPC ............................ G01N 27/121; H01L 51/524
See application file for complete search history.

(56) References Cited

U.S. PATENT DOCUMENTS

| | | | | |
|---|---|---|---|---|
| 2005/0184661 A1* | 8/2005 | Chiu | .................... | G01N 27/121 313/512 |
| 2008/0007163 A1* | 1/2008 | Matsuura | ............ | H01L 51/5253 313/504 |
| 2015/0362449 A1* | 12/2015 | Suzuki | ................. | G01N 27/121 257/40 |

\* cited by examiner

*Primary Examiner* — Farun Lu
(74) *Attorney, Agent, or Firm* — Kinney & Lange, P.A.

(57) ABSTRACT

The present application provides a package structure, a method for manufacturing the same, a method for detecting a package defect in the package structure, an OLED device, and a display apparatus. The package structure includes: a first cover plate and a second cover plate; a sealant disposed between the first cover plate and the second cover plate and configured to form a sealed space with the first cover plate and the second cover plate; a moisture detection portion located in the sealed space; a first electrode having one terminal connected to a portion of the moisture detection portion, and the other terminal extending beyond the sealed space; and a second electrode having one terminal connected to another portion of the moisture detection portion, and the other terminal extending beyond the sealed space.

12 Claims, 9 Drawing Sheets

PACKAGE STRUCTURE, METHOD FOR MANUFACTURING THE SAME, METHOD FOR DETECTING PACKAGE DEFECT, OLED DEVICE AND DISPLAY APPARATUS

CROSS-REFERENCE TO RELATED APPLICATION

This application claims priority to Chinese Patent Application No. 201711350463.0, filed on Dec. 25, 2017, which is incorporated herein by reference in its entirety.

BACKGROUND

The present disclosure relates to the field of packaging technologies, and more particularly, to a package structure, a method for manufacturing the same, a method for detecting a package defect, an Organic Light Emitting Diode (OLED) device, and a display apparatus.

In a process of packaging an OLED, an upper cover plate and a lower cover plate are fixed together through a sealant. However, when the OLED is practically packaged, due to the quality of the sealant itself or the operation of the packaging process, there may be defects generated at the sealant, which enables external moisture and the like to enter the inside of the package through the defects, and thus has adverse effects on electronic devices in the package. Therefore, it needs to detect such package defects and eliminate the package defects in time. The related detection methods are mainly performed by measuring a width of the sealant, observing a picture after lighting, using the discoloration effect of the water-absorbing substance, etc. These methods have low detection efficiency, need artificial observation, and have a high human cost.

SUMMARY

The present disclosure proposes a package structure, a method for manufacturing the same, a method for detecting a package defect, an OLED device, and a display apparatus.

According to an aspect of the present disclosure, there is provided a package structure. The package structure comprises: a first cover plate and a second cover plate; a sealant disposed between the first cover plate and the second cover plate and configured to form a sealed space with the first cover plate and the second cover plate; a moisture detection portion located in the sealed space; a first electrode having one terminal connected to a portion of the moisture detection portion, and the other terminal extending beyond the sealed space; and a second electrode having one terminal connected to another portion of the moisture detection portion, and the other terminal extending beyond the sealed space.

In an embodiment, the moisture detection portion comprises water-absorbing detection material and resistivity of the moisture detection portion changes after water absorption.

In an embodiment, the package structure comprises a plurality of first electrodes and a plurality of second electrodes.

In an embodiment, the plurality of first electrodes are disposed in parallel between the moisture detection portion and the first cover plate, and the plurality of second electrodes are disposed in parallel between the moisture detection portion and the second cover plate.

In an embodiment, the plurality of first electrodes and the plurality of second electrodes are alternately disposed between the first cover plate and the moisture detection portion. In another embodiment, the plurality of first electrodes and the plurality of second electrodes are alternately disposed between the second cover plate and the moisture detection portion.

In an embodiment, the package structure further comprises an insulating layer, wherein when the plurality of first electrodes and the plurality of second electrodes are alternately disposed between the second cover plate and the moisture detection portion, the insulating layer is disposed between the first cover plate and the moisture detection portion, wherein via holes are formed in the insulating layer, the plurality of second electrodes are disposed between the insulating layer and the moisture detection portion, and the plurality of first electrodes are disposed between the insulating layer and the first cover plate and are electrically connected to the moisture detection portion through the via holes. When the plurality of first electrodes and the plurality of second electrodes are alternately disposed between the second cover plate and the moisture detection portion, the insulating layer is disposed between the second cover plate and the moisture detection portion, wherein via holes are formed in the insulating layer, the plurality of second electrodes are disposed between the insulating layer and the moisture detection portion, and the plurality of first electrodes are disposed between the insulating layer and the second cover plate and are electrically connected to the moisture detection portion through the via holes.

In an embodiment, the moisture detection portion comprise a metal ion compound.

In an embodiment, the package structure is configurable to package Organic Light-Emitting Diode (OLED).

According to another aspect of the present disclosure, there is provided a method for manufacturing a package structure. The method comprises: providing a first cover plate and a second cover plate; forming a first electrode and a second electrode on at least one of the first cover plate and the second cover plate; forming a moisture detection portion and a sealant on one of the first cover plate and the second cover plate; and interfacing the first cover plate to the second cover plate, so that in the package structure after the cover plates are interfaced, the sealant, the first cover plate and the second cover plate form a sealed space, the moisture detection portion is located in the sealed space, the first electrode has one terminal connected to a portion of the moisture detection portion, and the other terminal extending beyond the sealed space, and the second electrode has one terminal connected to another portion of the moisture detection portion, and the other terminal extending beyond the sealed space.

In an embodiment, forming the first electrode and the second electrode on at least one of the first cover plate and the second cover plate comprises: forming a plurality of first electrodes and a plurality of second electrodes.

In an embodiment, forming the first electrode and the second electrode on at least one of the first cover plate and the second cover plate further comprises: forming the plurality of first electrodes so that the plurality of first electrodes are disposed in parallel on the first cover plate, and forming the plurality of second electrodes so that the plurality of second electrodes are disposed in parallel on the second cover plate.

In an embodiment, forming the first electrode and the second electrode on at least one of the first cover plate and the second cover plate further comprises: forming the plurality of first electrodes and the plurality of second electrodes so that the plurality of first electrodes and the plurality of second electrodes are alternately disposed on the first cover plate. In another embodiment, forming the first electrode and the second electrode on at least one of the first cover plate and the second cover plate further comprises: forming the plurality of first electrodes and the plurality of second electrodes so that the plurality of first electrodes and the plurality of second electrodes are alternately disposed on the second cover plate. In an embodiment, the method further comprises: forming an insulating layer on the first cover plate or the second cover plate. When the plurality of first electrodes and the plurality of second electrodes which are alternately disposed are formed on the second cover plate, the method comprises: forming the plurality of first electrodes on the first cover plate; forming an insulating layer on the first cover plate, so that the insulating layer covers the first electrodes; and forming the second electrodes on the insulating layer, and forming via holes in the insulating layer, so that the first electrodes can be electrically connected to the moisture detection portion through the via holes; and when the plurality of first electrodes and the plurality of second electrodes which are alternately disposed are formed on the second cover plate, the method comprises: forming the plurality of first electrodes on the second cover plate; forming an insulating layer on the second cover plate, so that the insulating layer covers the plurality of first electrodes; and forming the plurality of second electrodes on the insulating layer, and forming via holes in the insulating layer, so that the first electrodes can be electrically connected to the moisture detection portion through the via holes.

In an embodiment, the package structure is configurable to package Organic Light-Emitting Diode (OLED).

According to yet another aspect of the present disclosure, there is provided a method for detecting a package defect in the package structure according to the above embodiments. The method comprises: connecting the first electrode and the second electrode to a detection circuit to form a loop, detecting, by the detection circuit, current in the loop, and determining if there is a package defect in the package structure by comparing the current in the loop with a current threshold.

According to yet another aspect of the present disclosure, there is further provided an Organic Light-Emitting Diode (OLED) device. The OLED device comprises the package structure according to the above embodiments. One of the first cover plate and the second cover plate is a substrate of the OLED, and the other is at least one of a package layer, a passivation layer, a resist layer or a cap layer.

According to yet another aspect of the present disclosure, there is further provided a display apparatus. The display apparatus comprises the OLED device according to the above embodiments.

BRIEF DESCRIPTION OF THE DRAWINGS

The above and other purposes, features and advantages of the present disclosure will become more apparent from the following description of the embodiments of the present disclosure with reference to the accompanying drawings.

DETAILED DESCRIPTION

Exemplary embodiments of the present disclosure will be described in detail below with reference to the accompanying drawings. Throughout the accompanying drawings, the same elements are denoted by the same or similar reference signs. In the following description, some specific embodiments are for illustrative purposes only, and should not to be construed as limiting the present disclosure, but are examples of the embodiments of the present disclosure. Conventional structures or configurations will be omitted when they may cause confusion to the understanding of the present disclosure. It should be illustrated that shapes and sizes of various components in the accompanying drawings do not reflect true sizes and proportions, but merely illustrate contents of the embodiments of the present disclosure.

References to "one embodiment", "an embodiment", "one example" or "an example" in the whole specification mean that particular features, structures, or characteristics described in connection with the embodiment or example are included in at least one embodiment of the present disclosure. Therefore, appearances of phrases "in one embodiment", "in an embodiment", "one example" or "an example" at various places in the whole specification does not necessarily refer to the same embodiment or example. Furthermore, particular features, structures, or characteristics may be combined in one or more embodiments or examples in any suitable combination and/or sub-combination.

It should also be illustrated that those skilled in the art can understand that the terms "A is connected with B" and "A is connected to B" herein may be that A is directly connected to B, or A is connected to B through one or more other components. In addition, "connected with" and "connected to" herein may be physical electrical connections, or may be electrical coupling or electrical couplings etc.

According to an embodiment of the present disclosure, there is provided a package structure. The package structure comprises a first cover plate, a second cover plate, a sealant, a moisture detection portion, a first electrode and a second electrode. Here, the sealant form a sealed space with the first cover plate and the second cover plate. The moisture detection portion is located in the sealed space. The first electrode has one terminal connected to a portion of the moisture detection portion, and the other terminal extending beyond the sealed space. The second electrode has one terminal connected to another portion of the moisture detection portion, and the other terminal extending beyond the sealed space.

A package structure according to a plurality of embodiments of the present disclosure will be described in detail below with reference to FIGS. 1 to 4D.

Figure 1:
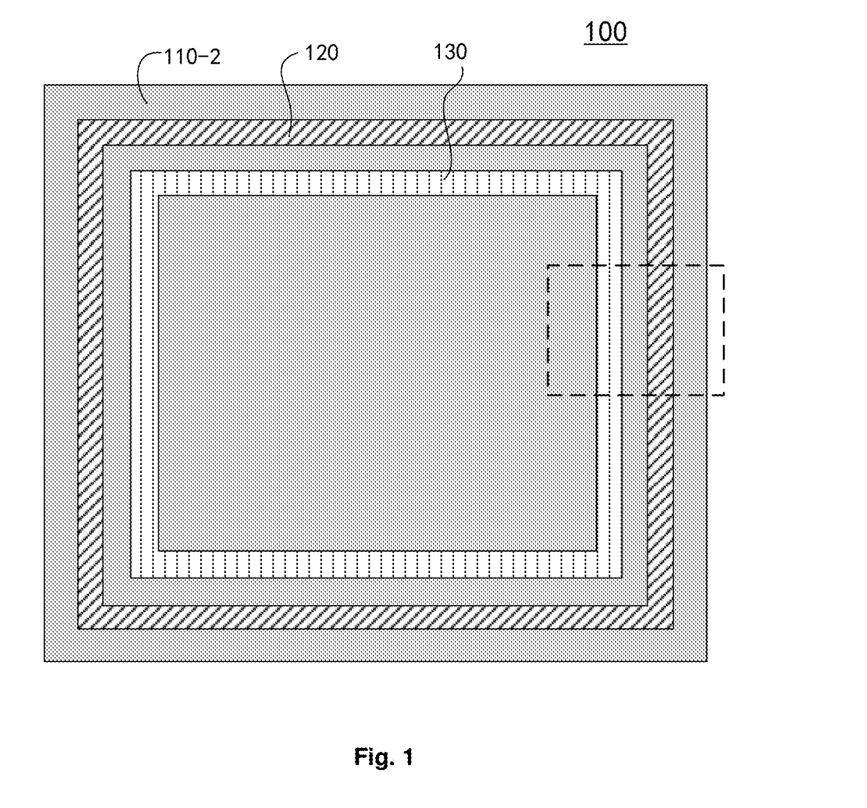
FIG. 1 illustrates a schematic top cross-sectional view of a package structure according to an embodiment of the present disclosure.

FIG. 1 illustrates a schematic top cross-sectional view of a package structure 100 according to an embodiment of the present disclosure. A second cover plate 110-2, and a sealant 120 and a moisture detection portion 130 between a first cover plate and the second cover plate are shown in FIG. 1. FIG. 1 illustrates a positional relationship of the sealant 120 and the moisture detection portion 130 on the cover plate from an overall perspective, wherein illustration of a first electrode and a second electrode is omitted for the sake of brevity. The cross-sectional view shown in FIG. 1 is taken from a plane passing through the sealant 120 and the moisture detection portion 130 and parallel to the cover plate. It can be seen from FIG. 1 that, the sealant 120 forms a sealed space with the first cover plate and the second cover plate, and the moisture detection portion 130 is located in the sealed space.

The elements being packaged in the package structure 100 (e.g. OLED) can be disposed in the sealed space formed by the cover plates 110-1 and 110-2 and sealant 120.

In one embodiment, where the packaged elements are OLEDs, one of the first cover plate 110-1 and the second cover plate 110-2 can be used as the substrate of the OLED, and the other can be used as at least one of a package layer, a passivation layer, a resist layer or a cap layer that covers the OLED.

In FIG. 1, the sealant 120 is shown as a frame-shaped structure, and the moisture detection portion 130 is also shown as a frame-shaped structure. Each side of the moisture detection portion 130 extends in the same direction as a corresponding side of the sealant 120. It should be understood that the shapes of the sealant 120 and the moisture detection portion 130 are not limited thereto. In other embodiments, the sealant 120 may be formed into other shapes, such as a circular frame, a triangular frame, or any shape which adapts to a shape of the cover plate, and the moisture detection portion 130 may be formed into a circular frame, a triangular frame, or any shape which adapts to the shape of the sealant 120. In some embodiments, the moisture detection portion 130 may be formed into a plurality of separate portions instead of a continuous structure as in FIG. 1. In some embodiments, the moisture detection portion 130 may also be in direct contact with the sealant 120 instead of having a certain gap with the sealant as in FIG. 1.

In one embodiment, the moisture detection portion 130 comprises water-absorbing detection material. The water-absorbing detection material is a material of which a value of a specific property changes after water absorption, wherein the specific property may be an electromagnetic property, an optical property, a thermal property, a mechanical property etc. In one embodiment, a resistivity of the water-absorbing detection material changes after water absorption. For example, the water-absorbing detection material may be a material which is non-conductive when it is dry but has a certain electrical conductivity after water absorption. Further, in one embodiment, the electrical conductivity of the water-absorbing detection material is proportional to an amount of water absorption. Examples of the water-absorbing detection material comprise metal ion compounds such as NaCl, KCl, NaNO$_3$, KNO$_3$, etc. In one embodiment, the water-absorbing detection material may be provided by magnetron sputtering, evaporation, printing, etc.

It should be understood that, the term "dry" used herein should be interpreted in a broad sense, and generally refer to a status where the water-absorbing detection material have not crystalized into a new structure or new substance by absorbing water or moisture. Thus, the term "dry" does not necessarily indicate an absolute dry status with no moisture being absorbed in the water-absorbing detection material.

Figure 2A:
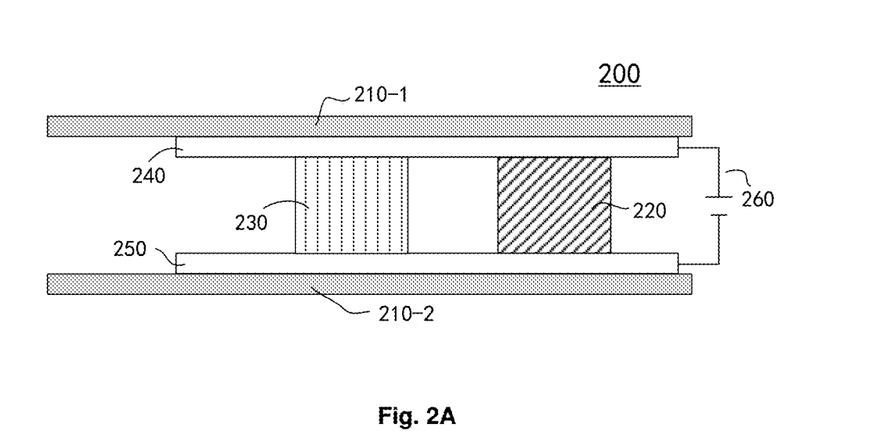
FIG. 2A is a side cross-sectional view of a portion of a package structure according to an embodiment of the present disclosure.
Figure 2B:
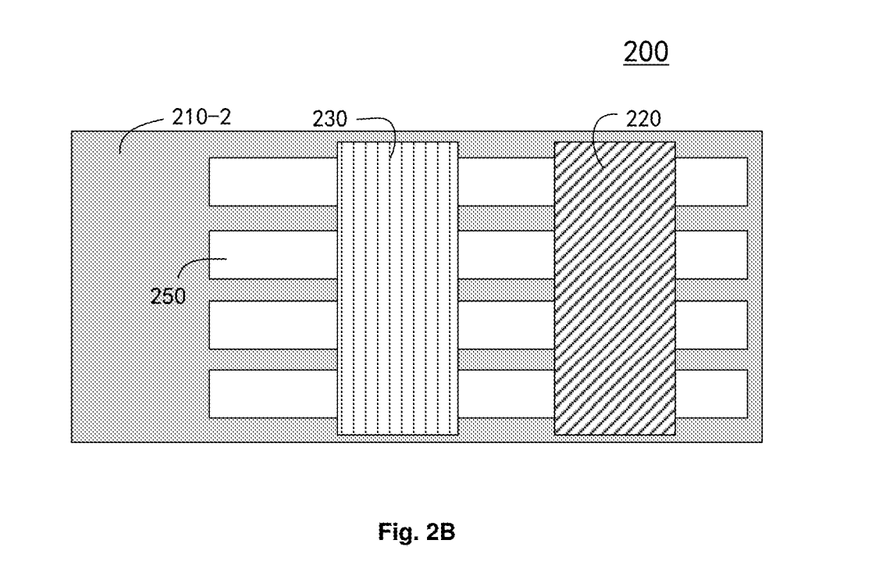
FIG. 2B is a top cross-sectional view of a portion of a package structure according to an embodiment of the present disclosure.

FIGS. 2A-2D illustrate structural diagrams of a portion of a package structure 200 according to an embodiment of the present disclosure. A portion of the package structure 200 shown in FIGS. 2A-2D is for example a portion defined by a dashed box in FIG. 1. Here, FIG. 2A is a side cross-sectional view of a portion of the package structure 200 according to an embodiment of the present disclosure, and FIG. 2B is a top cross-sectional view of a portion of the package structure 200 according to an embodiment of the present disclosure.

As shown, the package structure 200 comprises a first cover plate 210-1, a second cover plate 210-2, a sealant 220, a moisture detection portion 230, a first electrode 240, and a second electrode 250.

The sealant 220 is connected to the first cover plate 210-1 and the second cover plate 210-2, and forms a sealed space with the first cover plate 210-1 and the second cover plate 210-2 (FIGS. 2A and 2B do not illustrate the entire sealed space since they are partial schematic views). The moisture detection portion 230 is located in the sealed space.

The first electrode 240 is an upper electrode between the moisture detection portion 230 and the first cover plate 210-1, and has one terminal connected to the top of the moisture detection portion 230, and the other terminal extending beyond the sealed space.

The second electrode 250 is a lower electrode between the moisture detection portion 230 and the second cover plate 210-2, and has one terminal connected to the bottom of the moisture detection portion 230, and the other terminal extending beyond the sealed space.

In FIGS. 2A and 2B, terminals of the first electrode 240 and the second electrode 250 which are located in the sealed space protrude from the inside of the moisture detection portion 230. It should be understood that this structure is merely exemplary, and in other embodiments, it is possible that the terminals of the first electrode 240 and the second electrode 250 do not protrude from the inside of the moisture detection portion 230 as long as the connection between the first electrode 240 and the moisture detection portion 230 and the connection between the second electrode 250 and the moisture detection portion 230 are ensured.

It can be seen from FIG. 2B that, the second electrode 250 comprises a plurality of electrodes disposed in parallel along an extending direction of the sealant 220, and any two of the plurality of second electrodes are electrically insulated from each other. Similarly, the first electrode 240 also comprises a plurality of electrodes disposed in parallel along the extending direction of the sealant 220, and any two of the plurality of first electrodes are electrically insulated from each other. In one embodiment, the plurality of second electrodes are disposed in one-to-one correspondence with the plurality of first electrodes.

It should be understood that in other embodiments, the first electrode 240 and the second electrode 250, as the upper electrode and the lower electrode respectively, may have other arrangements, for example, one upper electrode corresponds to a plurality of lower electrodes or one lower electrode corresponds to a plurality of upper electrodes.

In general, the denser the arrangement of the first electrodes and the second electrodes, the higher the degree of fineness in detecting the package defect, but the higher the manufacturing cost and the manufacturing complexity. In order to compromise between these two factors, an appropriate electrode arrangement density may be set according to detection requirements or product specifications.

A detection circuit 260 is also shown in FIG. 2A. The first electrode 240 extends beyond an end portion of the sealed space and the second electrode 250 extends beyond the end portion of the sealed space as test terminals to be connected to the detection circuit 260. In the case shown in FIGS. 2A and 2B, there is no defect at the sealant 220, and therefore the moisture detection portion 230 is dry, and at this time the moisture detection portion 230 has no electrical conductivity (or has a large resistivity). At this time, there is no current (or the current does not exceed a defined threshold) in a loop formed by connecting the first electrode, the second electrode, and the moisture detection portion to the detection circuit 260.

Figure 2C:
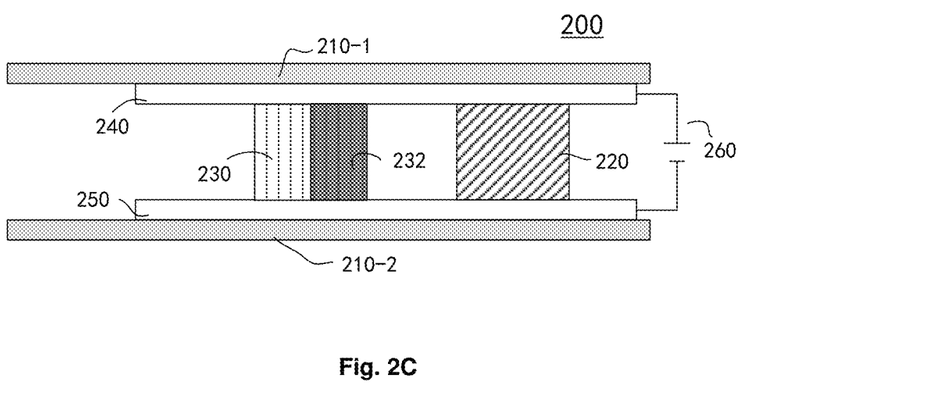
FIG. 2C is a schematic side cross-sectional view of a portion of a package structure in a case where there is a defect at a sealant according to an embodiment of the present disclosure.
Figure 2D:
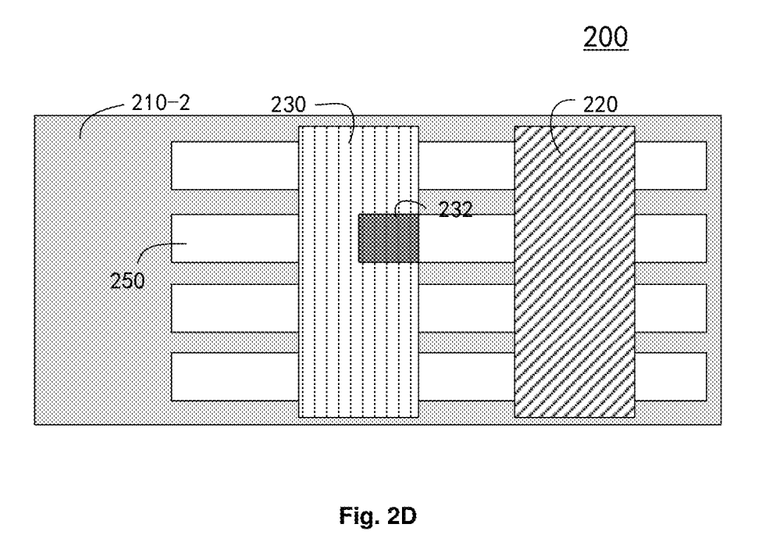
FIG. 2D is a schematic top cross-sectional view of a portion of a package structure in a case where there is a defect at a sealant according to an embodiment of the present disclosure.

FIG. 2C is a schematic side cross-sectional view of a portion of the package structure 200 in a case where there is a defect at the sealant according to an embodiment of the present disclosure, and FIG. 2D is a schematic top cross-sectional view of a portion of the package structure 200 in a case where there is a defect at the sealant according to an embodiment of the present disclosure. Compared with FIGS. 2A and 2B, FIGS. 2C and 2D differ in that as there is a defect at the sealant 220, moisture enters the sealed space from the outside of the package, and thus a portion of the moisture detection portion 230 is no longer dry due to water absorption, for example, as indicated by a dark portion 232 in the figures. The portion 232 of the moisture detection portion 230 has electrical conductivity due to water absorption, and therefore when the first electrode 240 extends beyond the end portion of the sealed space and the second electrode 250 extends beyond the end portion of the sealed space as test terminals to be connected to the detection circuit 260, the formed loop is turned on, it can be detected that there is current (or the current exceeds a defined threshold), and thereby it can be determined that a portion of the sealant of the package structure 200 at a detection position has a defect.

In another embodiment, the current detected by the detection circuit 260 is compared with a current threshold, and when the current detected in the detection circuit 260 exceeds the defined threshold, it is determined that the portion of the sealant of the package structure 200 at the detection position has a defect. The setting of the current threshold can reduce false alarms due to detection errors or other factors.

Figure 3A:
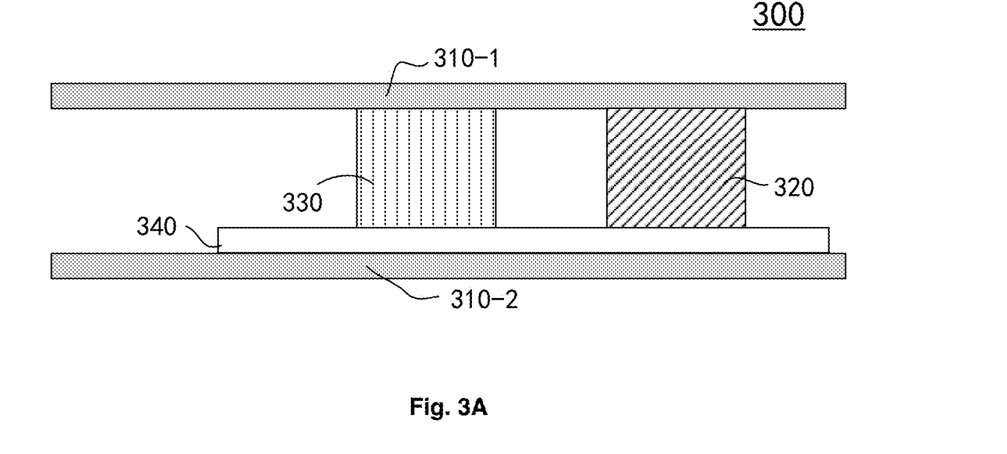
FIG. 3A is a side cross-sectional view of a portion of a package structure according to another embodiment of the present disclosure.
Figure 3B:
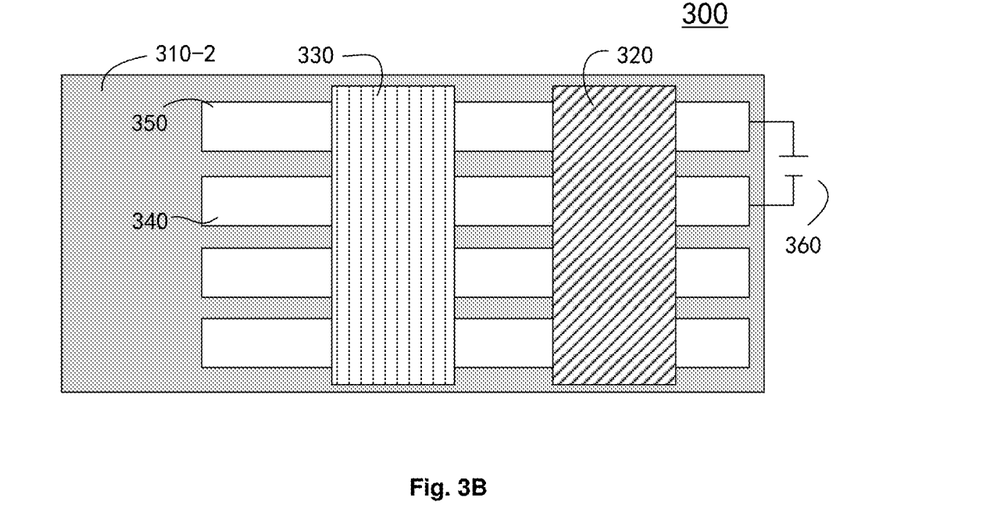
FIG. 3B is a top cross-sectional view of a portion of a package structure according to another embodiment of the present disclosure.

FIGS. 3A-3D illustrate structural diagrams of a portion of a package structure 300 according to another embodiment of the present disclosure. A portion of the package structure 300 shown in FIGS. 3A-3D is the portion defined by the dashed box in FIG. 1. Here, FIG. 3A is a side cross-sectional view of a portion of the package structure 300 according to an embodiment of the present disclosure, and FIG. 3B is a top cross-sectional view of a portion of the package structure 300 according to an embodiment of the present disclosure.

As shown, the package structure 300 comprises a first cover plate 310-1, a second cover plate 310-2, a sealant 320, a moisture detection portion 330, a first electrode 340, and a second electrode 350.

The sealant 320 is connected to the first cover plate 310-1 and the second cover plate 310-2, and forms a sealed space with the first cover plate 310-1 and the second cover plate 310-2 (FIGS. 3A and 3B do not illustrate the entire sealed space since they are partial schematic views). The moisture detection portion 330 is located in the sealed space.

The first electrode 340 is disposed between the second cover plate 310-2 and the moisture detection portion 330, and has one terminal extending beyond the sealed space.

The second electrode 350 is also disposed between the second cover plate 310-2 and the moisture detection portion 330, and has one terminal extending beyond the sealed space.

In the package structure 300, a plurality of first electrodes 340 and a plurality of second electrodes 350 are alternately disposed on the second cover plate 310-2.

It should be understood that in other embodiments, the first electrode 340 and the second electrode 350 may also be disposed between the first cover plate 310-1 and the moisture detection portion.

In FIGS. 3A and 3B, terminals of the first electrode 340 and the second electrode 350 which are located in the sealed space protrude from the inside of the moisture detection portion 330. It should be understood that this structure is merely exemplary, and in other embodiments, it is possible that the terminals of the first electrode 340 and the second electrode 350 do not protrude from the inside of the moisture detection portion 330 as long as the connection between the first electrode 340 and the moisture detection portion 330 and the connection between the second electrode 350 and the moisture detection portion 330 are ensured.

A detection circuit 360 is also shown in FIG. 3B. A second portion 340-2 of the first electrode 340 extends beyond an end portion of the sealed space and the second electrode 350 extends beyond the end portion of the sealed space as test terminals to be connected to the detection circuit 360. In the case shown in FIGS. 3A and 3B, there is no defect at the sealant 320, and therefore the moisture detection portion 330 is dry, and at this time the moisture detection portion 330 has no electrical conductivity (or has a large resistivity). At this time, there is no current (or the current does not exceed a defined threshold) in a loop formed by connecting the first electrode, the second electrode, and the moisture detection portion to the detection circuit 360.

Figure 3C:
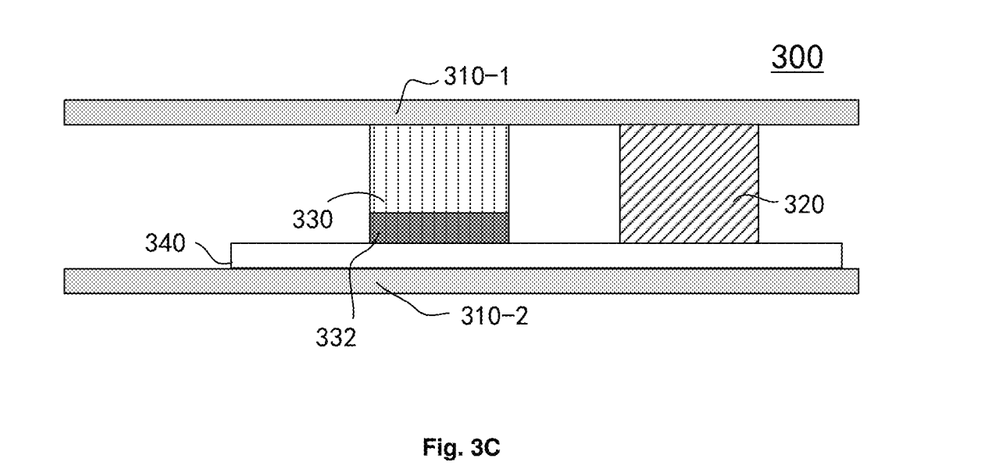
FIG. 3C is a schematic side cross-sectional view of a portion of a package structure in a case where there is a defect at a sealant according to another embodiment of the present disclosure.
Figure 3D:
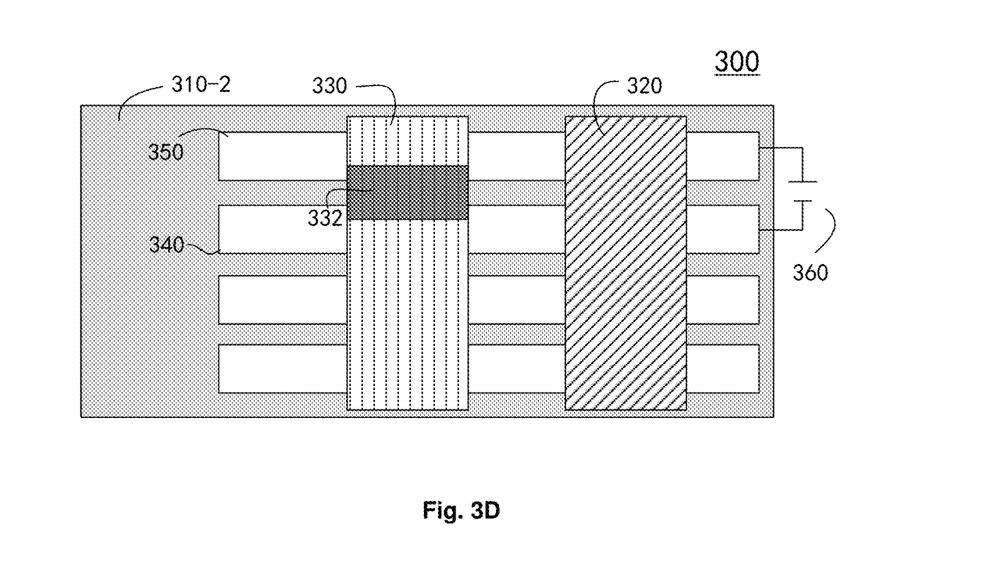
FIG. 3D is a schematic top cross-sectional view of a portion of a package structure in a case where there is a defect at a sealant according to another embodiment of the present disclosure.

FIG. 3C is a schematic side cross-sectional view of a portion of the package structure 300 in a case where there is a defect at the sealant according to an embodiment of the present disclosure, and FIG. 3D is a schematic top cross-sectional view of a portion of the package structure 300 in a case where there is a defect at the sealant according to an embodiment of the present disclosure. Compared with FIGS. 3A and 3B, FIGS. 3C and 3D differ in that as there is a defect at the sealant 320, moisture enters the sealed space from the outside of the package, and thus a portion of the moisture detection portion 330 is no longer dry due to water absorption, for example, as indicated by a dark portion 332 shown in the figures. The portion 332 of the moisture detection portion 330 has electrical conductivity due to water absorption, and therefore when the first electrode 340 extends beyond the end portion of the sealed space and the second electrode 350 extends beyond the end portion of the sealed space as test terminals to be connected to the detection circuit 360, the formed loop is turned on, it can be detected that there is current (or the current exceeds a defined threshold), and thereby it can be determined that a portion of the sealant 320 of the package structure 300 at a detection position has a defect.

In another embodiment, the current detected by the detection circuit 360 is compared with a current threshold, and when the current detected in the detection circuit 360 exceeds the defined threshold, it is determined that the portion of the sealant of the package structure 300 at the detection position has a defect. The setting of the current threshold can reduce false alarms due to detection errors or other factors.

Figure 4A:
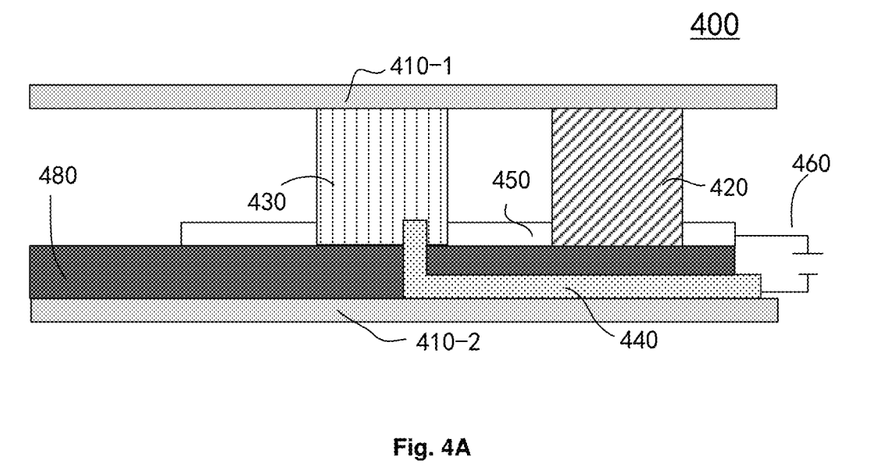
FIG. 4A is a side cross-sectional view of a portion of a package structure according to yet another embodiment of the present disclosure.
Figure 4B:
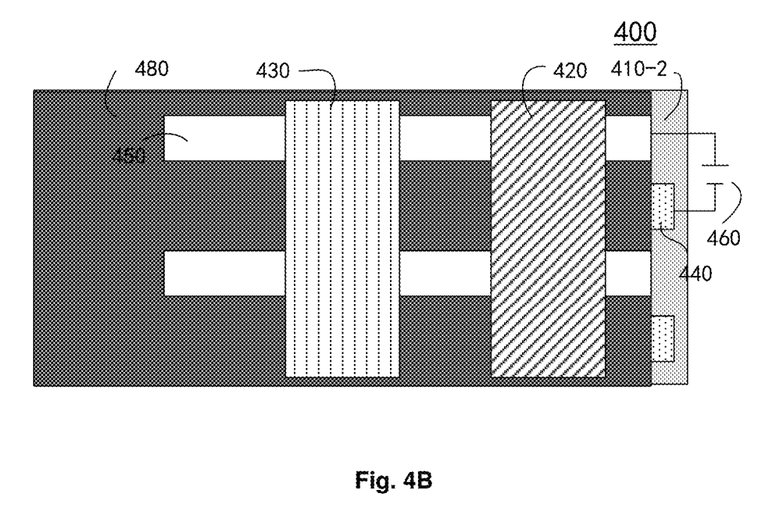
FIG. 4B is a top cross-sectional view of a portion of a package structure according to yet another embodiment of the present disclosure.

FIGS. 4A-4D illustrate structural diagrams of a portion of a package structure 400 according to another embodiment of the present disclosure. A portion of the package structure 400 shown in FIGS. 4A-4D is the portion defined by the dashed box in FIG. 1. Here, FIG. 4A is a side cross-sectional view of a portion of the package structure 400 according to an embodiment of the present disclosure, and FIG. 4B is a top cross-sectional view of a portion of the package structure 400 according to an embodiment of the present disclosure.

As shown, the package structure 400 comprises a first cover plate 410-1, a second cover plate 410-2, a sealant 420, a moisture detection portion 430, a first electrode 440, a second electrode 450, and an insulating layer 480.

Compared with the embodiment shown in FIGS. 3A-3B, the embodiment shown in FIG. 4A-4B differs in that an insulating layer 480 is added between the moisture detection portion 430 and the second cover plate 410-2.

The sealant 420 is disposed between the insulating layer 480 and the first cover plate 410-1 and forms a sealed space with the first cover plate 410-1 and the second cover plate 410-2 (FIGS. 4A and 4B do not illustrate the entire sealed space since they are partial schematic views). The moisture detection portion 430 is located in the sealed space.

The first electrode 440 is disposed between the second cover plate 310-2 and the insulating layer 480, and has one terminal extending beyond the sealed space, and the other terminal protruding from a surface of the insulating layer 480 through a via hole provided in the insulating layer 480 to be electrically connected to the moisture detection portion 430.

The second electrode 450 is disposed between the insulating layer 480 and the moisture detection portion 430, and has one terminal extending beyond the sealed space.

In the package structure 400, a plurality of first electrodes 440 and a plurality of second electrodes 450 are alternately disposed on the second cover plate 410-2.

It should be understood that in other embodiments, the first electrode 440 and the second electrode 450 may also be disposed between the first cover plate 410-1 and the moisture detection portion 430. When the first electrode 440 and the second electrode 450 are disposed between the first cover plate 410-1 and the moisture detection portion 430, the insulating layer 480 may also be disposed between the moisture detection portion 430 and the first cover plate 410-1.

In FIGS. 4A and 4B, a terminal of the second electrode 450 which is located in the sealed space protrudes from the inside of the moisture detection portion 430, and the moisture detection portion 430 covers the via hole in the insulating layer 480. It should be understood that this structure is merely exemplary, and in other embodiments, it is possible that the terminal of the second electrode 450 does not protrude from the inside of the moisture detection portion 430, and the moisture detection portion 430 does not cover the via hole in the insulating layer 480 as long as the connection between the first electrode 440 and the moisture detection portion 430 and the connection between the second electrode 450 and the moisture detection portion 430 are ensured.

A detection circuit 460 is also shown in FIGS. 4A and 4B. The first electrode 440 extends beyond an end portion of the sealed space and the second electrode 450 extends beyond the end portion of the sealed space as test terminals to be connected to the detection circuit 460. In the case shown in FIGS. 4A and 4B, there is no defect at the sealant 420, and therefore the moisture detection portion 430 is dry, and at this time the moisture detection portion 430 has no electrical conductivity (or has a large resistivity). At this time, there is no current (or the current does not exceed a defined threshold) in a loop formed by connecting the first electrode, the second electrode, and the moisture detection portion to the detection circuit 460.

Figure 4C:
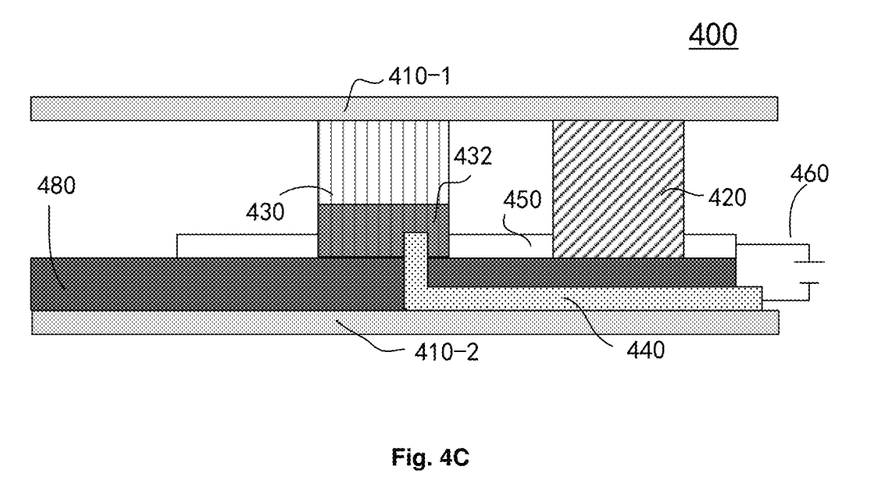
FIG. 4C is a schematic side cross-sectional view of a portion of a package structure in a case where there is a defect at a sealant according to yet another embodiment of the present disclosure.
Figure 4D:
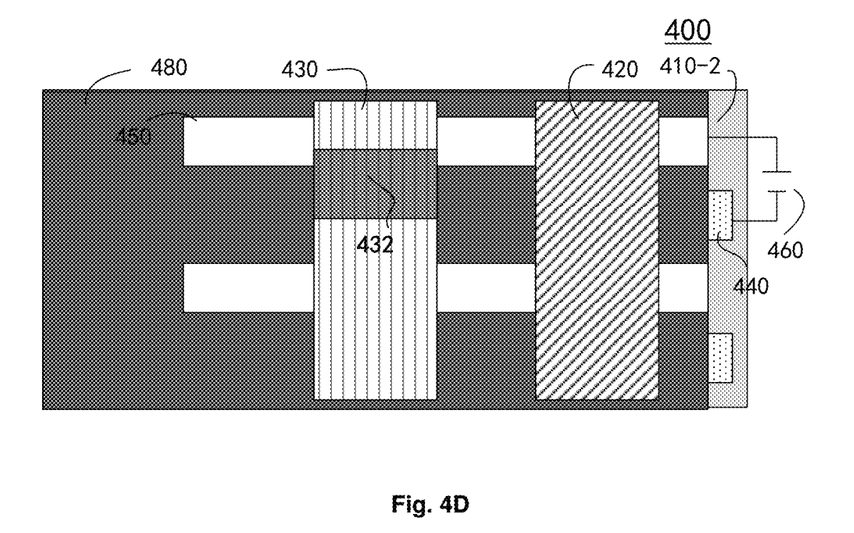
FIG. 4D is a schematic top cross-sectional view of a portion of a package structure in a case where there is a defect at a sealant according to yet another embodiment of the present disclosure.

FIG. 4C is a schematic side cross-sectional view of a portion of the package structure 400 in a case where there is a defect at the sealant according to an embodiment of the present disclosure, and FIG. 4D is a schematic top cross-sectional view of a portion of the package structure 400 in a case where there is a defect at the sealant according to an embodiment of the present disclosure. Compared with FIGS. 4A and 4B, FIGS. 4C and 4D differ in that as there is a defect at the sealant 420, moisture enters the sealed space from the outside of the package, and thus a portion of the moisture detection portion 430 is no longer dry due to water absorption, for example, as indicated by a dark portion 432 shown in the figures. The portion 432 of the moisture detection portion 430 has electrical conductivity due to water absorption, and therefore when the first electrode 440 extends beyond the end portion of the sealed space and the second electrode 450 extends beyond the end portion of the sealed space as test terminals to be connected to the detection circuit 460, the formed loop is turned on, it can be detected that there is current (or the current exceeds a defined threshold), and thereby it can be determined that a portion of the sealant 420 of the package structure 400 at a detection position has a defect.

In another embodiment, the current detected by the detection circuit 460 is compared with a current threshold, and when the current detected in the detection circuit 460 exceeds the defined threshold, it is determined that the portion of the sealant of the package structure 400 at the detection position has a defect. The setting of the current threshold can reduce false alarms due to detection errors or other factors.

In a practical detection process, it needs to connect a terminal of each of the first electrode and the second electrode which extends beyond the end portion of the sealed space to the detection circuit (or referred to as a detection Integrated Circuit (IC)) through leads. As a size of the detection circuit is much less than that covered by each of the electrodes to be detected, all of the leads tend to extend from connection terminals of corresponding electrodes toward the detection circuit in a convergence manner. In the package structure 400, the insulating layer 480 is added so that the first electrode 440 and the second electrode 450 are located on an upper surface and a lower surface of the insulating layer 480 respectively. Thus, when the leads converge from the corresponding electrodes toward the detection circuit, a lead from the first electrode 440 and a lead from the second electrode 450 have a certain gap therebetween in a direction perpendicular to a plane of the cover plate, which can avoid occurrence of a short circuit therebetween to ensure the smooth progress of the detection.

Figure 5:
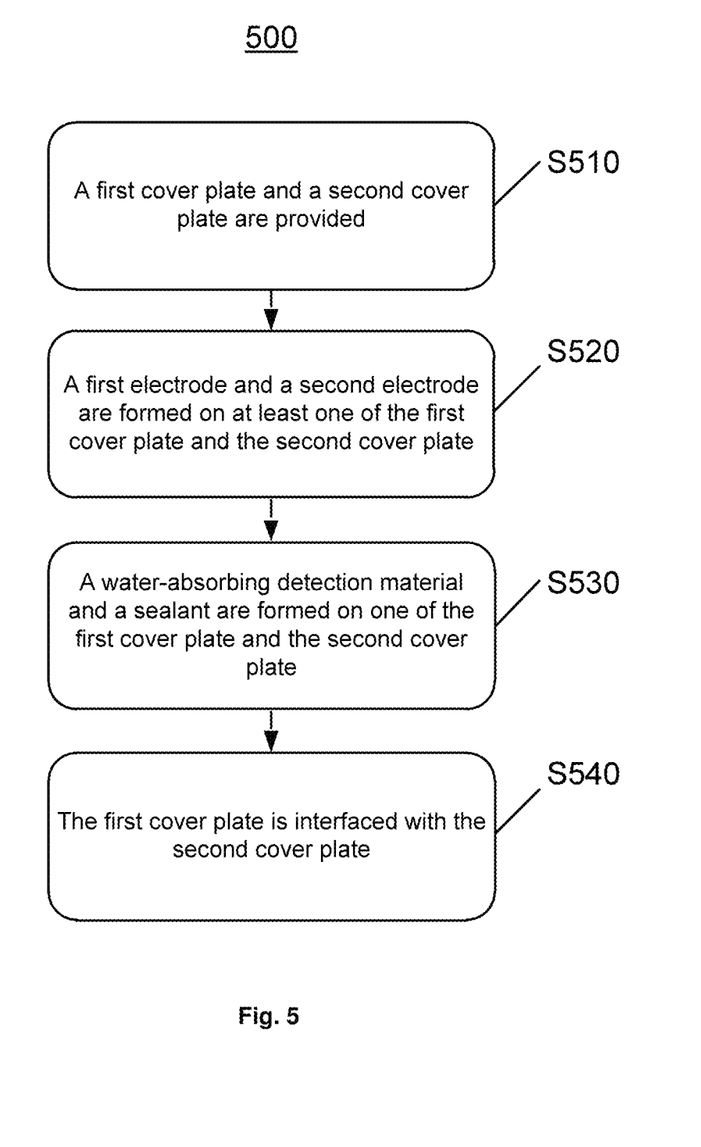
FIG. 5 illustrates a flowchart of a method for manufacturing a package structure according to an embodiment of the present disclosure.

FIG. 5 illustrates a flowchart of a method 500 for manufacturing a package structure according to an embodiment of the present disclosure.

As shown in FIG. 5, the method 500 starts at step S510, in which a first cover plate and a second cover plate are provided.

Then, in step S520, a first electrode and a second electrode are formed on at least one of the first cover plate and the second cover plate.

In one embodiment, step S520 may comprise forming the first electrode on the first cover plate and forming the second electrode on the second cover plate. Specifically, a plurality of parallel first electrodes may be formed on the first cover plate, and correspondingly, a plurality of parallel second electrodes may be formed on the second cover plate. Here, any two of the plurality of first electrodes are electrically insulated from each other, and any two of the plurality of second electrodes are also electrically insulated from each other. The method 500 according to this embodiment may be used to manufacture the package structure 200 as described above.

In another embodiment, step S520 may comprise alternately forming the first electrodes and the second electrodes on the first cover plate or the second cover plate (for example, in a predetermined direction). Method 500 according to this embodiment may be used to manufacture the package structure 300 as described above.

Next, in step S530, a moisture detection portion and a sealant are formed on one of the first cover plate and the second cover plate.

In one embodiment, step S530 may comprise forming the moisture detection portion and the sealant on the cover plate (i.e., the first cover plate or the second cover plate) formed with the first electrodes and the second electrodes which are alternately disposed, so that the moisture detection portion is electrically connected to the first electrode and the second electrode.

Finally, in step S540, the first cover plate is interfaced with the second cover plate, so that in the package structure after the cover plates are interfaced, the sealant forms a sealed space with the first cover plate and the second cover plate, the moisture detection portion is located in the sealed space, the first electrode has one terminal connected to a portion of the moisture detection portion, the other terminal extending beyond the sealed space, and the second electrode has one terminal connected to another portion of the moisture detection portion, and the other terminal extending beyond the sealed space.

In one embodiment, the method 500 may further comprise forming an insulating layer on the first cover plate or the second cover plate. Specifically, this step may be combined with step S520.

For example, when the first electrodes and the second electrodes which are alternately disposed are formed on the first cover plate, step S520 may comprise: forming the first electrodes on the first cover plate; forming an insulating layer on the first cover plate, so that the insulating layer covers the first electrodes; and forming the second electrodes on the insulating layer, and forming via holes in the insulating layer, so that the first electrodes can be electrically connected to the moisture detection portion through the via holes.

As another example, when the first electrodes and the second electrodes which are alternately disposed are formed on the second cover plate, step S520 may comprise: forming the first electrodes on the second cover plate; forming an insulating layer on the second cover plate, so that the insulating layer covers the first electrodes; and forming the second electrodes on the insulating layer, and forming via holes in the insulating layer, so that the first electrodes can be electrically connected to the moisture detection portion through the via holes.

Method 500 according to this embodiment may be used to manufacture the package structure 400 as described above.

It should be illustrated that the above description does not limit an order of the steps or operations, and the order of various steps or various operations in the same step may be adjusted as needed.

Figure 6:
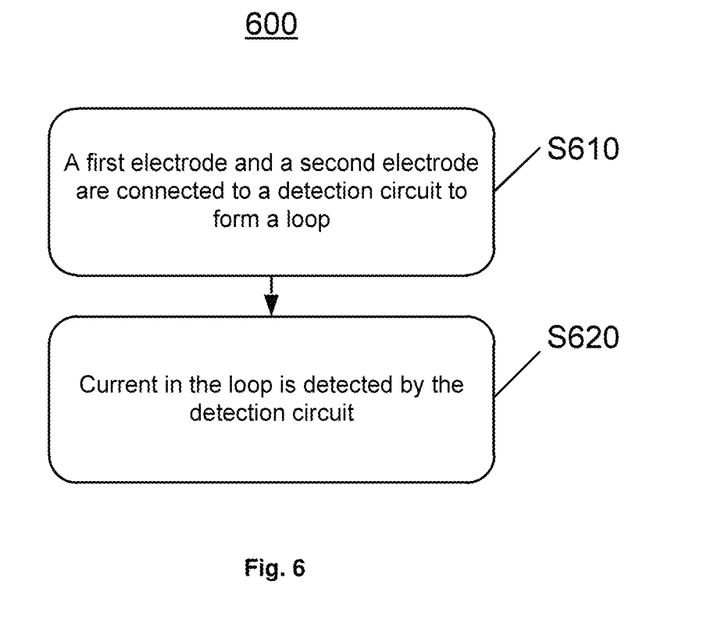
FIG. 6 illustrates a flowchart of a method for detecting a package defect in a package structure according to an embodiment of the present disclosure.

FIG. 6 illustrates a flowchart of a method 600 for detecting a package defect in the package structure 200, 300, or 400 according to an embodiment of the present disclosure.

As shown in FIG. 6, method 600 starts at step S610, in which a first electrode and a second electrode are connected to a detection circuit to form a loop.

Then, in step S620, current in the loop is detected by the detection circuit. Here, if it is detected in step S620 that the current in the loop is greater than a current threshold, it is determined that there is a package defect in the package structure.

The embodiments of the present disclosure further provide an OLED device. The OLED device comprises the package structure described according to the above embodiments. One of the first cover plate and the second cover plate is a substrate of the OLED, and the other is at least one of a package layer, a passivation layer, a resist layer or a cap layer.

The embodiments of the present disclosure further provide a display apparatus comprising the package structure according to the above embodiments. Specifically, the display apparatus may be a liquid crystal display apparatus such as a liquid crystal panel, a liquid crystal television, a mobile phone, an electronic reader, a liquid crystal display, etc.

The detailed description above has set forth numerous embodiments by using diagrams, flowcharts, and/or examples. In a case where such diagrams, flowcharts, and/or examples comprise one or more functions and/or operations, it should be understood by those skilled in the art that each function and/or operation in such diagrams, flowcharts, or examples can be implemented individually and/or together by various structures, hardware, software, firmware or substantially any combination thereof.

The present disclosure has been described with reference to a few exemplary embodiments, and it should be understood that the terms used are illustrative and exemplary and not restrictive. The present disclosure may be embodied in a variety of forms without departing from the spirit or substance of the present disclosure, and therefore it should be understood that the above-described embodiments are not limited to any detail above, and should be widely explained within the spirit and scope defined by the appended claims. Therefore, all changes and modifications which fall within the scope of the claims or the equivalents thereof are intended to be covered by the appended claims.

The invention claimed is:

1. A package structure, comprising:
   a first cover plate and a second cover plate;
   a sealant disposed between the first cover plate and the second cover plate and configured to form a sealed space with the first cover plate and the second cover plate;
   a moisture detection portion located in the sealed space;
   an insulation layer disposed between the first cover plate and the moisture detection portion, via holes being formed in the insulation layer;
   a plurality of first electrodes, wherein each of the plurality of first electrodes has a first terminal connected to a portion of the moisture detection portion, and a second terminal extending beyond the sealed space; and
   a plurality of second electrodes, wherein each of the plurality of second electrodes has a third terminal connected to another portion of the moisture detection portion, and a fourth terminal extending beyond the sealed space,
   wherein the plurality of first electrodes and the plurality of second electrodes are alternately disposed between the first cover plate and the moisture detection portion,
   wherein the plurality of second electrodes are disposed between the insulating layer and the moisture detection portion, and
   wherein the plurality of first electrodes are disposed between the insulating layer and the first cover plate and the plurality of first electrodes are electrically connected to the moisture detection portion through the via holes.

2. The package structure according to claim 1, wherein the moisture detection portion comprises water-absorbing detection material and resistivity of the moisture detection portion changes after water absorption.

3. The package structure according to claim 2, wherein the moisture detection portion comprise a metal ion compound.

4. The package structure according to claim 1, wherein the package structure is configurable to package Organic Light-Emitting Diode (OLED).

5. The package structure according to claim 4, wherein one of the first cover plate and the second cover plate is configurable to be used as a substrate of the OLED, and the other is configurable to be used as at least one of a package layer, a passivation layer, a resist layer or a cap layer that covers the OLED.

6. A method for manufacturing a package structure, comprising:
   providing a first cover plate and a second cover plate;
   forming a plurality of first electrodes and a plurality of second electrodes on the first cover plate so that the plurality of first electrodes and the plurality of second electrodes are alternately disposed on the first cover plate;
   forming a moisture detection portion and a sealant on one of the first cover plate and the second cover plate; and
   interfacing the first cover plate to the second cover plate, so that in the package structure after the cover plates are interfaced, the sealant, the first cover plate and the second cover plate form a sealed space, the moisture detection portion is located in the sealed space, each of the plurality of first electrodes has one terminal connected to a portion of the moisture detection portion, and another terminal extending beyond the sealed space, and each of the plurality of second electrodes has one terminal connected to another portion of the moisture detection portion, and another terminal extending beyond the sealed space,
   wherein forming the plurality of first electrodes and the plurality of second electrodes on the first cover plate, so that the plurality of first electrodes and the plurality of second electrodes are alternately disposed on the first cover plate comprises:
      forming the plurality of first electrodes on the first cover plate;
      forming an insulating layer on the first cover plate, so that the insulating layer covers the plurality of first electrodes; and
      forming the plurality of second electrodes on the insulating layer, and forming via holes in the insulating layer, so that the first electrodes can be electrically connected to the moisture detection portion through the via holes.

7. The method according to claim 6, wherein the package structure is configurable to package Organic Light-Emitting Diode (OLED).

8. The method according to claim 7, wherein one of the first cover plate and the second cover plate is configurable to be used as a substrate of the OLED, and the other is configurable to be used as at least one of a package layer, a passivation layer, a resist layer or a cap layer that covers the OLED.

9. A method for detecting a package defect in the package structure according to claim 1, comprising:
   connecting one of the plurality of first electrodes and one of the plurality of second electrodes to a detection circuit to form a loop,
   detecting, by the detection circuit, current in the loop, and
   determining if there is a package defect in the package structure by comparing the current in the loop with a current threshold.

10. A method for detecting a package defect in the package structure according to claim 2, comprising:
    connecting one of the first electrodes and one of the plurality of second electrodes to a detection circuit to form a loop,
    detecting, by the detection circuit, current in the loop, and
    determining if there is a package defect in the package structure by comparing the current in the loop with a current threshold.

11. An Organic Light-Emitting Diode (OLED) device, comprising the package structure according to claim 1.

12. An Organic Light-Emitting Diode (OLED) device, comprising the package structure according to claim 2.

* * * * *